(12) United States Patent
Croushorn et al.

(10) Patent No.: US 8,834,517 B2
(45) Date of Patent: Sep. 16, 2014

(54) PORTABLE PNEUMATIC ABDOMINAL AORTIC TOURNIQUET

(75) Inventors: John Croushorn, Hoover, AL (US); Richard Schwartz, Evans, GA (US)

(73) Assignee: Compression Works, LLC, Montgomery, AL (US)

( * ) Notice: Subject to any disclaimer, the term of this patent is extended or adjusted under 35 U.S.C. 154(b) by 417 days.

(21) Appl. No.: 12/150,728

(22) Filed: Apr. 30, 2008

(65) Prior Publication Data

US 2008/0281351 A1 Nov. 13, 2008

Related U.S. Application Data

(60) Provisional application No. 60/915,642, filed on May 2, 2007.

(51) Int. Cl.
*A61B 17/00* (2006.01)
*A61B 17/132* (2006.01)
*A61B 17/135* (2006.01)

(52) U.S. Cl.
CPC ........... *A61B 17/1325* (2013.01); *A61B 17/135* (2013.01)
USPC ....................................................... 606/203

(58) Field of Classification Search
USPC ................... 606/203, 202, 201, 204, 204.15, 606/204.25, 204.35; 600/490, 499; 601/151, 152; 602/53, 60–66, 75, 13, 602/41; 128/96.1, 869, 870
See application file for complete search history.

(56) References Cited

U.S. PATENT DOCUMENTS

| | | | |
|---|---|---|---|
| 1,679,978 A | 8/1928 | Konwiser et al. | |
| 2,660,174 A | 11/1953 | Saemann | |
| 4,635,635 A * | 1/1987 | Robinette-Lehman | 606/202 |
| 4,979,953 A * | 12/1990 | Spence | 606/202 |
| 5,193,549 A * | 3/1993 | Bellin et al. | 600/499 |
| 5,234,459 A * | 8/1993 | Lee | 606/203 |
| 5,295,996 A * | 3/1994 | Blair | 606/203 |
| 5,396,906 A * | 3/1995 | Harrold | 128/876 |
| 5,413,582 A * | 5/1995 | Eaton | 606/202 |
| 5,423,852 A * | 6/1995 | Daneshvar | 606/201 |
| 5,486,194 A * | 1/1996 | Kawasaki et al. | 606/203 |
| 5,514,155 A * | 5/1996 | Daneshvar | 606/201 |
| 5,628,721 A * | 5/1997 | Arnold et al. | 602/19 |
| 5,643,315 A | 7/1997 | Daneshvar | |
| 5,667,524 A * | 9/1997 | Bourgeois et al. | 606/202 |
| 5,695,520 A * | 12/1997 | Bruckner et al. | 606/204 |
| 5,792,173 A * | 8/1998 | Breen et al. | 606/201 |
| 5,871,499 A * | 2/1999 | Hahn et al. | 606/202 |
| 6,331,170 B1 * | 12/2001 | Ordway | 602/19 |
| 6,746,470 B2 | 6/2004 | McEwen et al. | |
| 6,884,254 B2 * | 4/2005 | Brooks | 606/201 |

(Continued)

*Primary Examiner* — Darwin Erezo
*Assistant Examiner* — Katrina Stransky
(74) *Attorney, Agent, or Firm* — The Gache Law Firm, P.C.; Russell C. Gache; Sara C. Kanos (NP)

(57) ABSTRACT

A portable pneumatic abdominal aortic tourniquet for occlusion of the abdominal descending aorta to restrict blood supply to a non-compressible arterial hemorrhage in the abdominal region. The tourniquet comprising an adjustable waist strap for securing around an abdomen; a directed air bladder mounted to the waist strap having a generally "V" shaped construction operable between a deflated condition wherein the directed air bladder is collapsed, and an inflated condition wherein the directed air bladder is expanded for exerting pressure against the abdomen; and, an air source connected to the directed air bladder for operating the directed air bladder between the deflated condition and the inflated condition.

28 Claims, 6 Drawing Sheets

(56) References Cited

U.S. PATENT DOCUMENTS

| | | |
|---|---|---|
| 6,960,223 B1 | 11/2005 | Ambach |
| 7,498,477 B2 * | 3/2009 | Wada et al. ............ 602/53 |
| 2003/0199922 A1 | 10/2003 | Buckman |
| 2004/0028540 A1 * | 2/2004 | Peck ............ 417/374 |
| 2004/0098035 A1 * | 5/2004 | Wada et al. ............ 606/201 |
| 2005/0113866 A1 | 5/2005 | Heinz et al. |
| 2005/0131326 A1 * | 6/2005 | Bates et al. ............ 602/41 |
| 2006/0095072 A1 | 5/2006 | TenBrink et al. |
| 2007/0191881 A1 | 8/2007 | Amisar et al. |

* cited by examiner

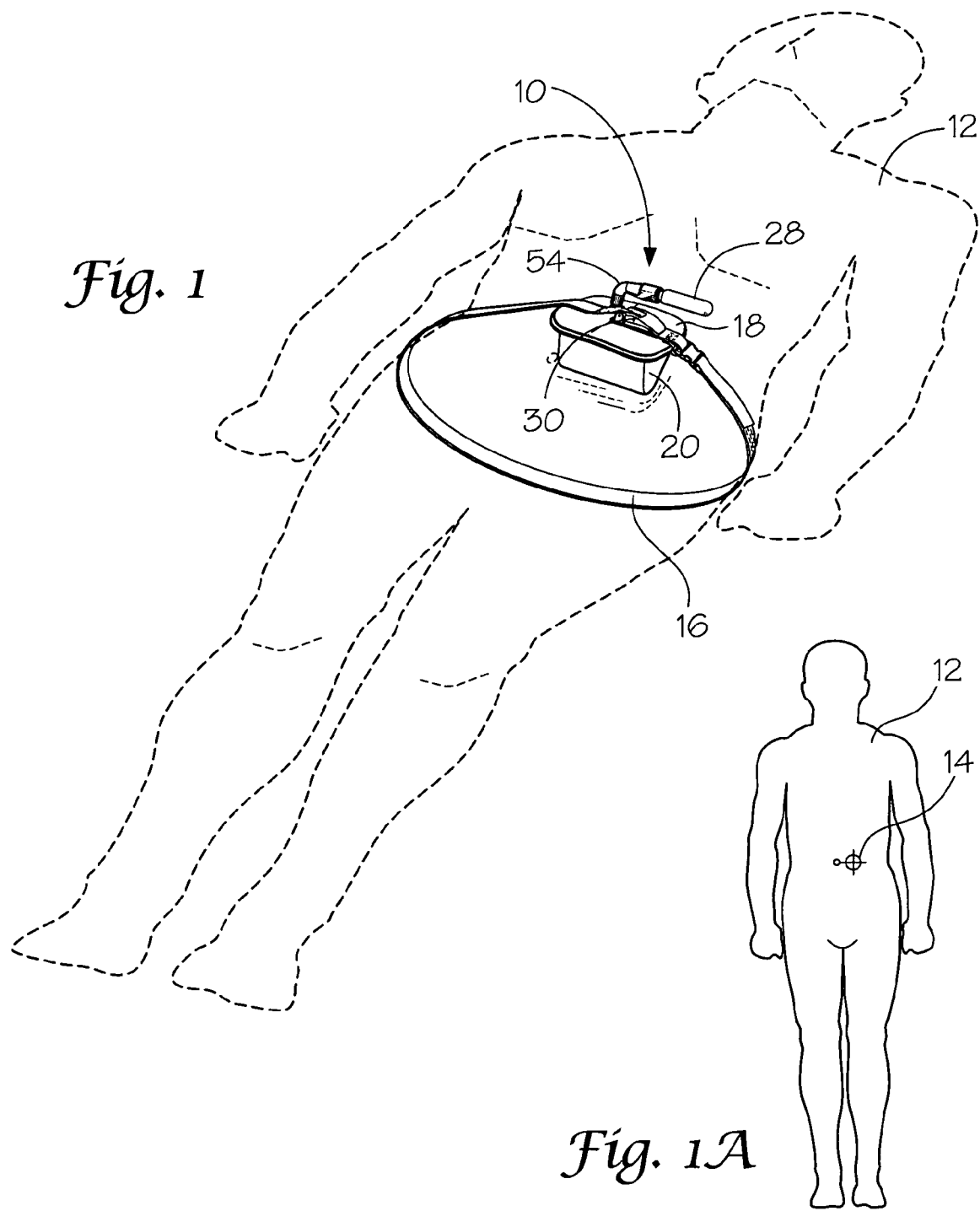

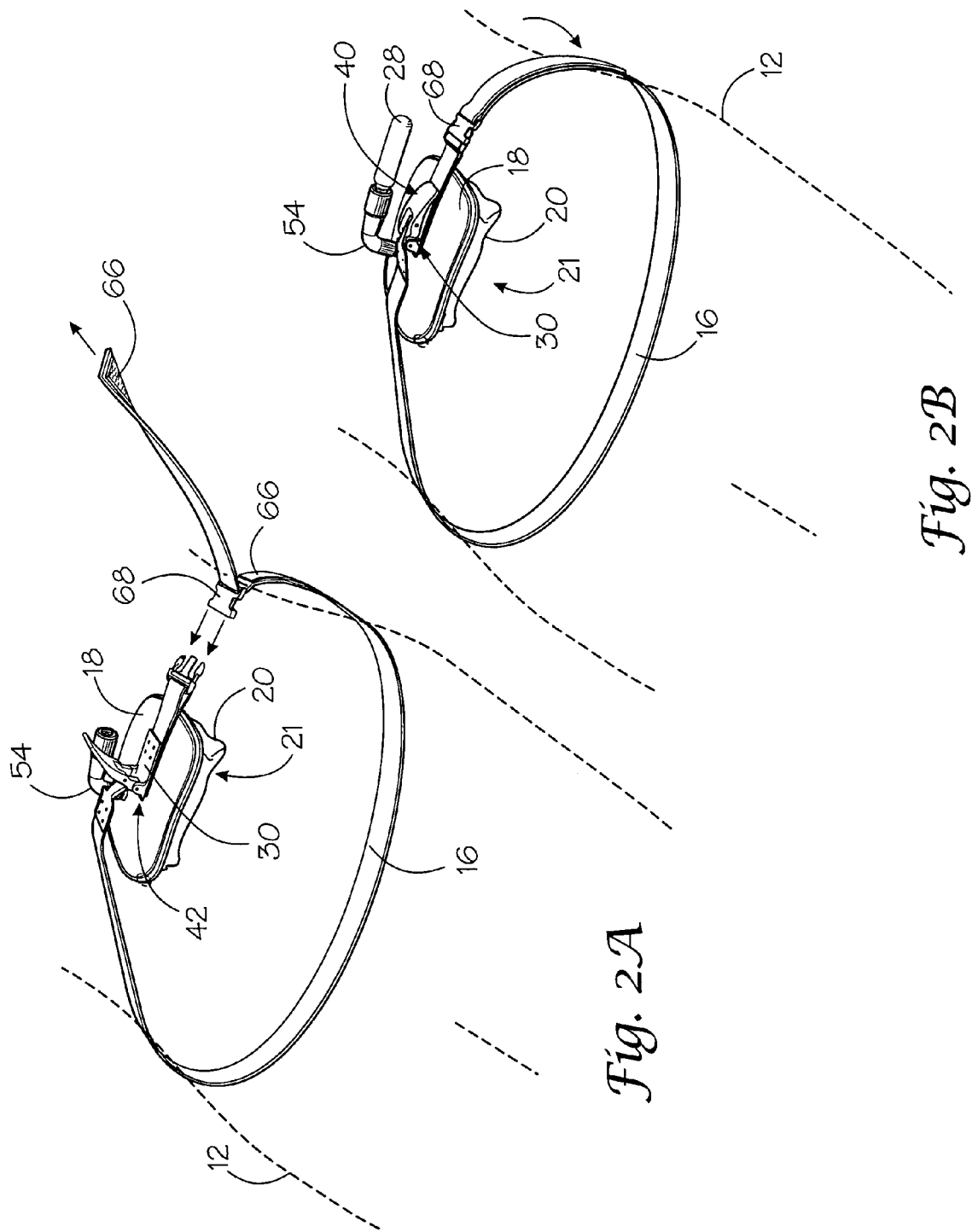

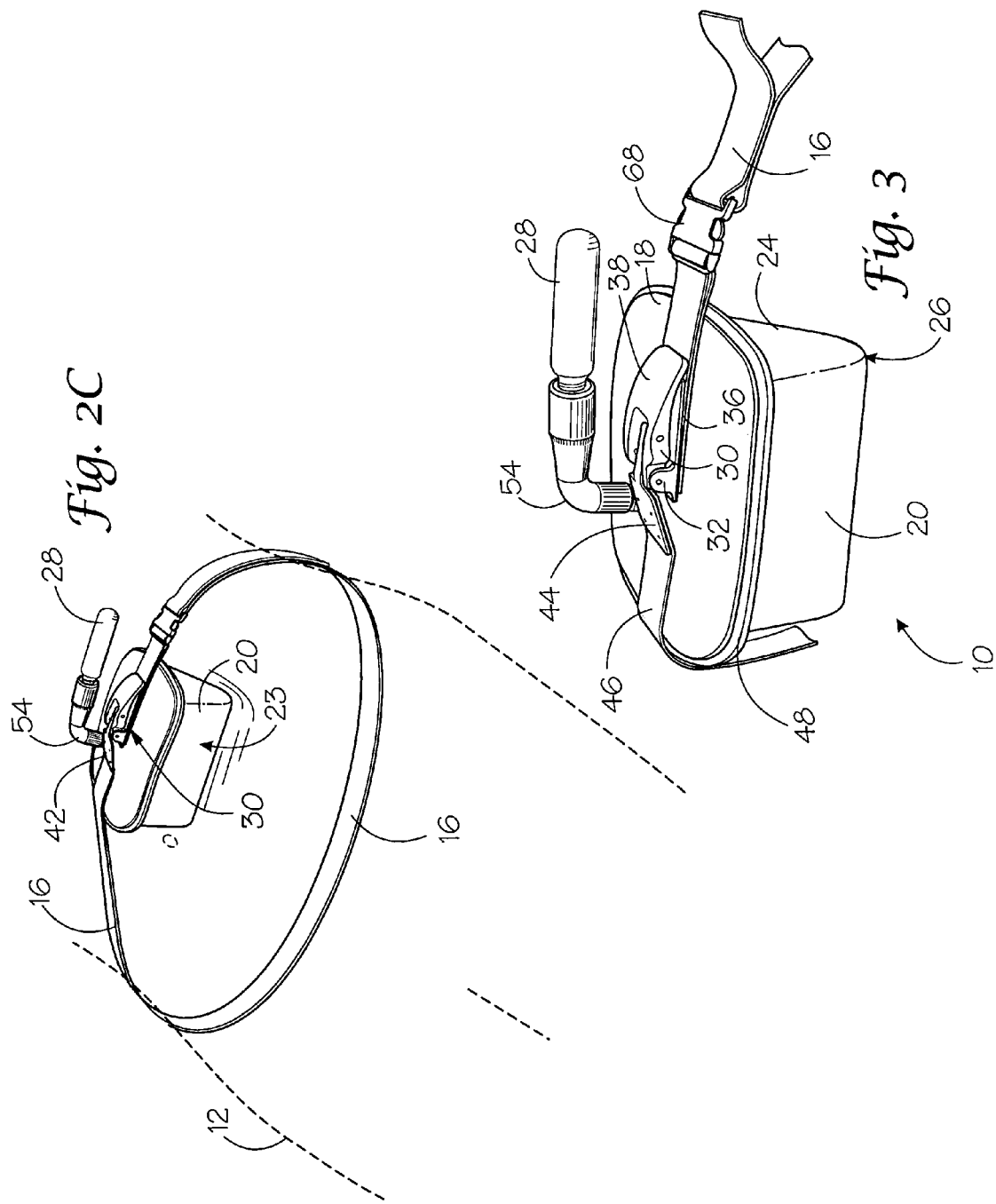

PORTABLE PNEUMATIC ABDOMINAL AORTIC TOURNIQUET

CROSS REFERENCE TO RELATED APPLICATION

This application claims priority from U.S. Provisional Application 60/915,642 filed May 2, 2007.

BACKGROUND OF THE INVENTION

1) Field of the Invention

The present invention relates to tourniquets, and more particularly, to a portable pneumatically operated aortic tourniquet device that consists of a waistband and an inflatable air bladder in combination with either a manual pump or a compressed gas injection cartridge for inflating the bladder. The air bladder is of a triangular shape so that a directed compression force is applied to the abdomen specifically to cut-off blood flow to the abdominal descending aorta.

2) Description of Related Art

The prior art is replete with various tourniquet devices that use a wide variety of clamping and/or pneumatic means to apply pressure to various limbs on the body. However, the prior art does not address the problems associated with abdominal aortic compression in the field in a rapid application portable package for restricting blood flow for a non-compressible arterial hemorrhage in the abdominal region. Such a wound requires occlusion of the abdominal descending aorta to cut-off the blood supply to the non-compressible arterial hemorrhage.

One of the major obstacles to providing an effective portable abdominal aortic tourniquet is in providing a focused compression force over a designated area on the abdomen. Typically, most tourniquets apply a constricting force around the circumference of a limb or over a broad area to reduce total blood flow through the limb. Such a broad application of force is ineffective to reduce or occlude blood flow through the descending aorta proximal to the bifurcation in the abdomen due to the deep location of the aorta in the body. A strong focused pressure is required to reach the descending aorta and reduce blood flow. The prior art fails to show or disclose a pneumatic tourniquet having a directed air bladder able to focus the compression force of the tourniquet sufficient to operate as an abdominal aortic tourniquet.

US Patent Application Publication No. 2007/0191881 A1 (Amisar et al.) shows a tourniquet that includes a pressure source and a selector leaver attached to cam to facilitate manual selection of a designated pressure. This tourniquet is designed to apply pressure around a limb. There is no teaching in the patent that this device would be effectively useable as an abdominal aortic tourniquet. Further, the air bladder is not a directed air bladder that would focus the compression force, but is rounded to wrap around the limb and spread the pressure force over a broad area. Such a broad application of constricting force is unusable if intended to reduce or occlude circulation through the descending aorta for a non-compressible arterial hemorrhage in the abdominal region.

U.S. Pat. No. 5,234,459 (Lee) shows an inflatable balloon for use in a tourniquet. The patent discloses a manual pump for inflating the balloon. There is no disclosure of the balloon having a directed shape for focusing a compression force, or that the tourniquet is in any way designed to work as an abdominal aortic tourniquet. This tourniquet is representative of a vast majority of pneumatic prior art tourniquet devices which completely fail to address the specific problems associated with providing an effective abdominal aortic tourniquet.

U.S. Pat. No. 6,884,254 (Brooks) shows a tourniquet system that includes a leverage assisted clamp means for tightening the strap around a limb. This patent is representative of a large section of the prior art that uses mechanical means, as opposed to pneumatic to provide a constricting force around a limb. Again, such devices fail to provide the directed compression force required to restrict blood flow through the descending aorta.

Accordingly, there is a need for a portable abdominal aortic tourniquet that can be rapidly applied under field conditions.

It is an object of the present invention to provide means for applying pressure on the exterior abdomen to reduce or occlude the flow of blood through the descending aorta proximal to the bifurcation.

It is an object of the present invention to provide a pneumatic device with sufficient compressing force to operate effectively as an abdominal aortic tourniquet.

It is an object of the present invention to provide a pneumatic tourniquet having a directed air bladder to focus a compressing force along a defined narrow section of the abdomen to reduce or occlude the flow of blood through the descending aorta proximal to the bifurcation.

It is an object of the present invention to provide an easily portable abdominal aortic pneumatic tourniquet that can be rapidly applied in the field.

SUMMARY OF THE INVENTION

The above objectives are accomplished according to the present invention by providing a pneumatic abdominal aortic tourniquet comprising an adjustable waist strap for securing around an abdomen; a rigid base plate carried by the waist strap having a width greater than the waist strap so that the base plate extends laterally outward from the waist strap to provide a stable base for positioning over a selected area of the abdomen; a directed air bladder carried on a bottom side of the base plate having a deflated condition wherein the directed air bladder is collapsed against the base plate, and an inflated condition wherein the directed air bladder is expanded to extend outwardly from the bottom side of the base plate; the directed air bladder having a generally "V" shaped construction so that a wide end of the directed air bladder is generally carried on the bottom side of the base plate and a narrow end of the directed air bladder presses against the abdomen when in the inflated condition so that a constricting force caused by inflation of the directed air bladder against the abdomen is focused against a narrow defined area of the abdomen to restrict blood flow through the abdominal aorta; and, an air source operatively connected in fluid communication with the directed air bladder for operating the directed air bladder between the deflated condition and the inflated condition.

In a further embodiment, the tourniquet includes a compression latch carried on the base plate operatively associated with the waist strap for tightening the waist strap around the abdomen. Preferably, the compression latch includes a latch base mounted to a top side of the base plate in a fixed arrangement with a first distal end of the waist strap; a latch arm pivotally mounted to the latch base operable between a closed position adjacent the latch base and an open position extending upward from the latch base; and, a terminal pivot arm pivotally carried by the latch arm having a second distal end of the waist strap secured thereto, wherein the terminal pivot arm is moved from a relaxed position to a tightened position when the latch arm is operated from the open position to the closed position so that the waist strap is shortened to tighten around the abdomen.

In a further embodiment, the tourniquet includes a foam pad carried on the bottom side of the base plate disposed between the directed air bladder and the base plate to cushion the base plate against the abdomen when the directed air bladder is in the deflated condition. Preferably, a peripheral edge of the foam pad extends beyond a peripheral edge of the base plate on all sides for cushioning against the abdomen before inflation of the directed air bladder.

In a further embodiment, the tourniquet includes a protective bladder sleeve surrounding the directed air bladder in both the inflated and collapsed conditions to resist puncture and protect against environmental exposure of the directed air bladder. Preferably, the protective bladder sleeve is attached to the directed air bladder so that the protective bladder sleeve is collapsed against the directed air bladder when the directed air bladder is in the deflated condition.

In a further embodiment, the tourniquet includes an inflation control valve carried by the air bladder in fluid communication with the air source and an interior cavity of the directed air bladder for controlling the flow of air into and out of the directed air bladder. Preferably, the inflation control valve is selected from the group consisting of a Presta valve and a Schrader valve. Further, it is preferred that the air source comprises a compressed gas cartridge.

In a further embodiment, the inflation control valve extends through the base plate for cooperating with the air source on a top side of the base plate. Preferably, an elbow connecting valve is disposed between the inflation control valve and the compressed gas cartridge so that the compressed gas cartridge extends generally parallel to the base plate when engaged with the elbow connecting valve.

In a further embodiment, the tourniquet includes a pressure relief valve operatively associated with the directed air bladder for adjusting an air pressure within the directed air bladder when in the inflated condition.

In an alternative embodiment, the air source includes a manual bulb pump having an air supply line connected to the directed air bladder in fluid communication for injecting air into the directed air bladder when the bulb pump is operated. Preferably, a pressure relief valve is carried by the air supply line for adjusting an air pressure within the directed air bladder when in the inflated condition.

In a further embodiment, the tourniquet includes at least one guide marker carried on the base plate for aligning the base plate on the abdomen over the abdominal aorta.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 1 shows a perspective view of a pneumatic abdominal aortic tourniquet attached in an operative condition to a person according to the present invention;

FIG. 1A shows a human form representation indicating where the pneumatic abdominal aortic tourniquet is to be applied according to the present invention;

FIG. 2A shows a perspective view of the pneumatic abdominal aortic tourniquet in a deflated condition being secured around a person's lower abdomen according to the present invention;

FIG. 2B shows a perspective view of the waist strap for the pneumatic abdominal aortic tourniquet secured around a person's lower abdomen according to the present invention;

FIG. 2C shows a perspective view of the pneumatic abdominal aortic tourniquet secured around a person's lower abdomen in an inflated condition according to the present invention;

FIG. 3 shows a detailed perspective view of the pneumatic abdominal aortic tourniquet according to the present invention;

DETAILED DESCRIPTION OF A PREFERRED EMBODIMENT

Figure 4A:
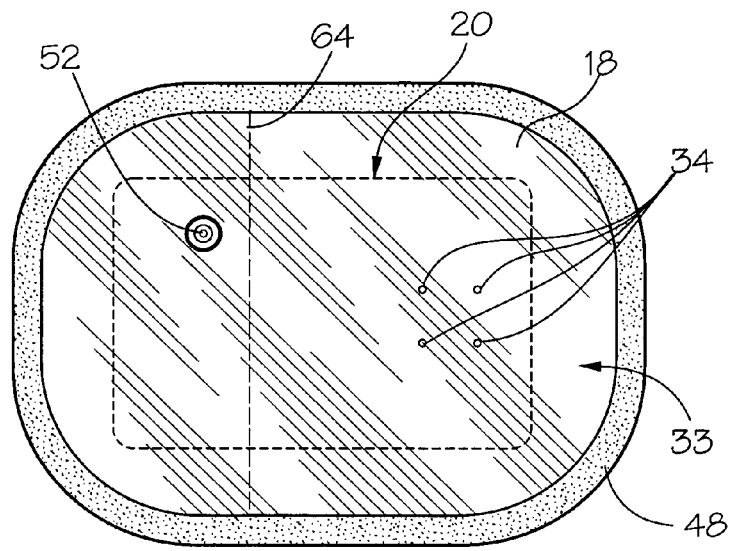
FIG. 4A shows a top plan view of the base plate of the pneumatic abdominal aortic tourniquet according to the present invention.

With reference to the drawings, the invention will now be described in more detail. Referring to FIG. 1, a pneumatic abdominal aortic tourniquet, designated generally as 10, is shown secured around the lower abdomen of a person 12 for restricting blood flow through the descending aorta proximal to the bifurcation to deal with a non-compressible arterial hemorrhage in the abdominal region. Referring to FIG. 1A, the tourniquet is arranged over the abdomen to apply localized pressure to pressure point 14 to restrict blood flow.

Referring to FIGS. 1 and 3, pneumatic abdominal aortic tourniquet 10 includes an adjustable waist strap 16 for securing around the abdomen. A rigid base plate 18 is carried on waist strap 16. Base plate 18 is constructed and arranged to have a width greater than waist strap 16 so that base plate 18 extends laterally outward from waist strap 16 to provide a stable base for positioning over a selected area, such as pressure point 14 (FIG. 1A), of the abdomen.

A directed air bladder 20 is carried on a bottom side 22 of base plate 18. As shown in FIGS. 2A and 2B, directed air bladder has a deflated condition, designated generally as 21, for initial installation wherein directed air bladder 20 is generally collapsed against base plate 18. Referring to FIG. 2C, directed air bladder 20 is then operated to an inflated condition, designated generally as 23, wherein directed air bladder 20 is expanded to extend outwardly from bottom side 22 (FIG. 4B) of base plate 18 to exert pressure on a localized area of the abdomen. Referring to FIG. 4C, directed air bladder 20 is constructed and arranged to have a generally elongated "V" or cuneiform shaped construction so that a wide end, designated generally as 24, of directed air bladder 20 is carried on bottom side 22 of base plate 18. A narrow end 26 of directed air bladder 20 presses against the abdomen when in the inflated condition (FIG. 2C) so that a constricting force caused by inflation of directed air bladder 20 against the abdomen is focused against a narrow defined area of the abdomen to restrict blood flow through the abdominal aorta.

Referring to FIG. 3, an air source 28 is operatively connected in fluid communication with directed air bladder 20 for operating the directed air bladder between deflated condition 21 and inflated condition 23. Preferably, air source 28 comprises a compressed gas cartridge, such as a $CO_2$ cartridge well known to those skilled in the art.

Referring to FIG. 3, tourniquet 10 may include a compression latch 30 carried on base plate 18 operatively associated with waist strap 16 for tightening waist strap 16 around the abdomen. Compression latch 30 is not necessary to practice the invention and is provided by way of example only as to a known method of further securing waist strap 16 in a tight arrangement around the user's abdomen as illustrated. Compression latch 30 can be useful particularly for larger user's where sufficiently tightening the waist strap may be difficult. Preferably, compression latch 30 includes a latch base 32 mounted to a top side 33 (FIG. 4B) of base plate 18 in a fixed arrangement. Referring to FIG. 4A, openings 34 may be included in base plate 18 for receiving rivets, screws or the like for mounting latch base 32 to top side 33 of base plate 18 in a secure arrangement. Referring to FIG. 3, in a preferred embodiment, a first distal end 36 of waist strap 16 is disposed between latch base 32 and top side 33 of base plate 18 to secure base plate 18 to waist strap 16. A latch arm 38 is pivotally mounted to latch base 32 and is operable between a closed position, designated generally as 40, wherein latch arm 38 is adjacent latch base 32, and an open position, designated generally as 42 (FIG. 2A), extending upward from latch base 32. A terminal pivot arm 44 is pivotally carried by latch arm 38 having a second distal end 46 of waist strap 16 secured thereto. Terminal pivot arm 44 moves from a relaxed position (FIG. 2A) when latch arm 38 is in open position 42, to a tightened position (FIGS. 2B and 2C) when latch arm 38 is moved to closed position 40 so that waist strap 16 is shortened to tighten around the abdomen.

Figure 4B:
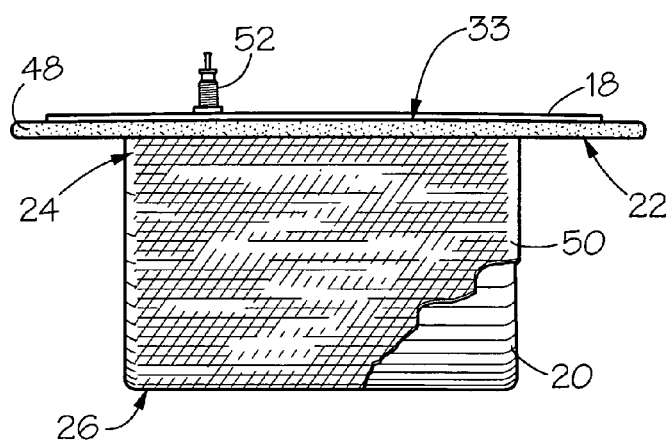
FIG. 4B shows a front elevation view and cut-away of the base plate carrying the inflatable air bladder and protective sleeve covering the air bladder according to the present invention.
Figure 4C:
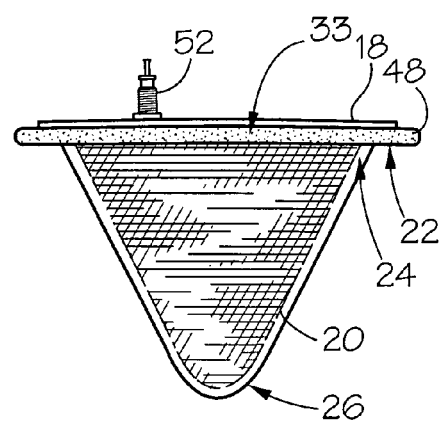
FIG. 4C shows a side elevation view of the base plate carrying the inflatable air bladder according to the present invention.

Referring to FIGS. 4A-4C, a foam pad 48 may be carried on bottom side 22 of base plate 18 disposed between directed air bladder 20 and base plate 18 to cushion base plate 18 against the abdomen when the directed air bladder is in deflated condition 21. Preferably, a peripheral edge of foam pad 48 extends beyond a peripheral edge of base plate 18 on all sides for cushioning against the abdomen before inflation of directed air bladder 20. Preferably, foam pad is 0.5 cm thick and extends beyond the edges of the base plate by 1 cm.

Referring to FIG. 4B, a protective bladder sleeve 50 may be provided surrounding directed air bladder 20 in both inflated and collapsed conditions 21 and 23 respectively, to resist puncture and protect against environmental exposure of directed air bladder 20. Preferably, protective bladder sleeve 50 is attached to directed air bladder 20, such as by using an adhesive or making protective bladder sleeve 50 form fitting, so that protective bladder sleeve 50 is collapsed against directed air bladder 20 when in deflated condition 21.

Referring to FIGS. 4A-4C, an inflation control valve 52 is carried by directed air bladder 20. Inflation control valve 52 is placed in fluid communication with air source 28 and an interior cavity of directed air bladder 20 for controlling the flow of air into and out of directed air bladder 20 for operation between inflated condition 23 and deflated condition 21. Preferably, inflation control valve 52 is a Presta valve or a Schrader valve. In the illustrated embodiment, inflation control valve 52 extends through base plate 18 for cooperating with air source 28 on top side 33 of base plate 18. In a further embodiment, a pressure gauge is operatively associated with directed air bladder 20 for warning if the pressure is dropping in the bladder or maximum pressure has been reached.

Figure 5A:
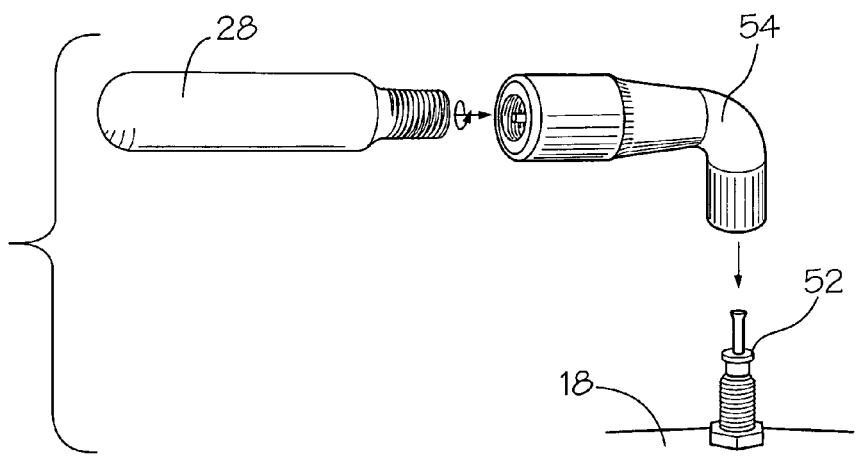
FIG. 5A shows a detailed exploded view of the air source, elbow connector and inflation control valve according to the present invention.

Referring to FIG. 5A, an elbow connecting valve 54 is preferably disposed between inflation control valve 52 and air source 28, in the form of a compressed gas cartridge, extends generally parallel to base plate 18 when engaged with elbow connecting valve 54. This provides a lower profile to the design to help avoid accidental contact with air source 28 that may result in disengagement and deflation of directed air bladder 20.

Figure 5B:
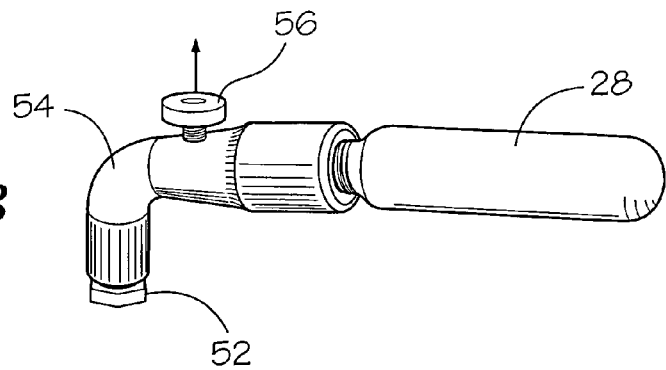
FIG. 5B shows an alternative embodiment of the elbow connector according to the present invention.

Referring to FIG. 5B, in a further embodiment, a pressure relief valve 56 is carried by elbow connecting valve 54 which is operatively associated with directed air bladder 20 through inflation control valve 52 for adjusting an air pressure within directed air bladder 20 when in inflated condition 23. Pressure relief valve 56 may alternatively be carried at an alternative location such as directly on air bladder 20, and is not limited to be disposed on elbow connecting valve 54, which is illustrated as the preferred location as a matter of convenient use.

Figure 6:
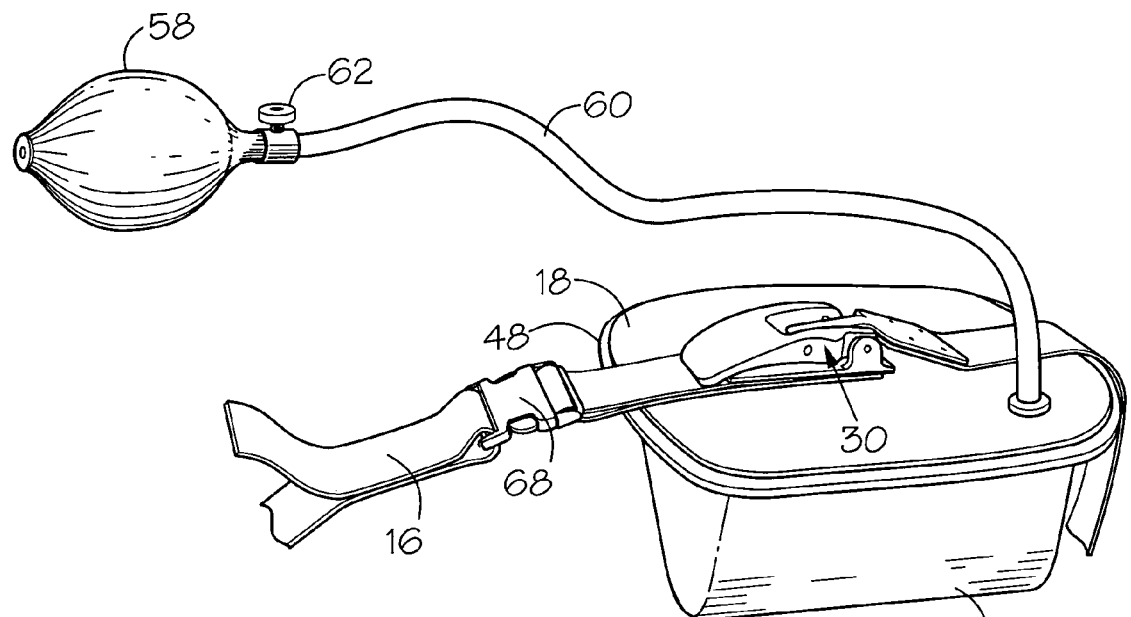
FIG. 6 shows an alternative embodiment of the pneumatic abdominal aortic tourniquet having an inflation bulb pump according to the present invention; and, FIG. 7 shows an alternative embodiment of the pneumatic abdominal aortic tourniquet having quick release inflation system and manual blow valve.

Referring to FIG. 6, in an alternative embodiment, air source 28 includes a manual bulb pump 58 and an air supply line 60 extending from bulb pump 58 to directed air bladder 20 through base plate 18 for injecting air into directed air bladder 20 when bulb pump 58 is operated. Preferably, a pressure relief valve 62 is carried by air supply line 60 for adjusting the air pressure within directed air bladder 20 when in inflated condition 23.

Figure 7:
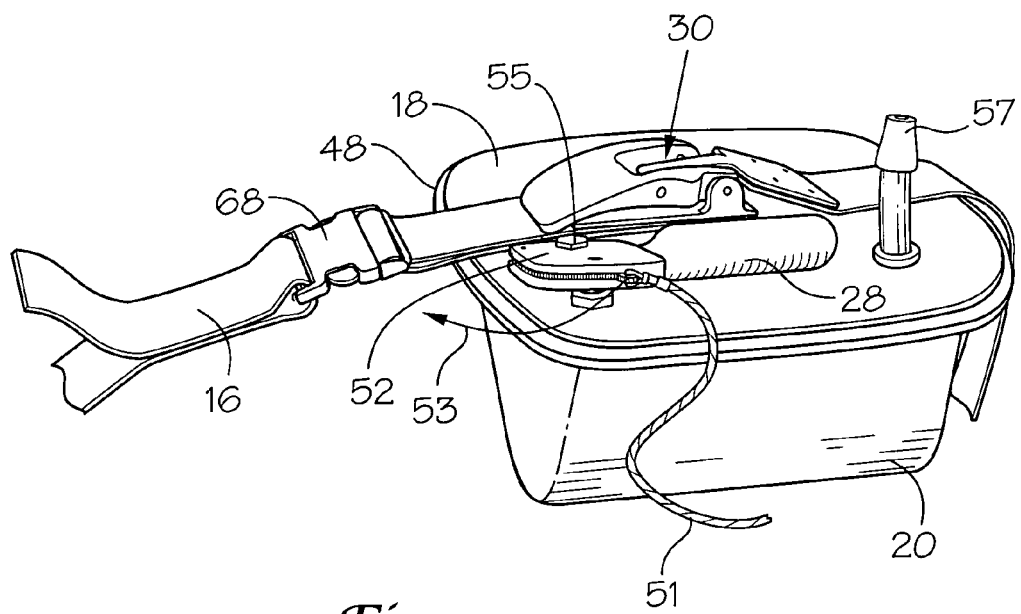

Referring to FIG. 7, a further alternative embodiment is shown in which air source 28 and inflation control valve 52 consist of a quick release inflation system well-known to those skilled in the art and commonly available. By pulling a release cord 51 in direction 53, a predetermined volume of air is injected from air cartridge 28 into directed air bladder 20. Preferably, a bleed valve 55 is provided to adjust the pressure when inflated against the user's abdomen. In a further embodiment, a manual inflation blow valve 57 can be used alone or in combination with the various inflation systems described herein to inflate directed air bladder 20. Preferable inflation blow valve 57 is a "bite valve" that opens when the person blowing on the valve bites down on the valve.

Referring to FIG. 4A, at least one guide marker 64 may be carried on base plate 18 for helping align base plate 18 on the abdomen over the abdominal aorta as indicated by pressure point 14 of FIG. 1A.

Preferably, waist strap 16 is constructed of 4 cm wide, 120 cm long, nylon webbing. Referring to FIGS. 2A and 2B, cooperating hook and loop fasteners 66 are preferably provided for securing loose ends of strap 16 onto itself once the strap is drawn tight around the abdomen. Waist strap 16 is of sufficient length to go around the torso just above the iliac crest. Referring to FIG. 3, a quick connect buckle 68 is provided on waist strap 16 for quickly attaching and detaching waist strap 16 around the torso.

Base plate 18 is preferably made of injected molded ridged plastic material. Base plate 18 serves a two fold: first, it is meant to connect the pressure application mechanism, directed air bladder 20, to waist strap 16, and; second, base plate 18 is to provide a stable platform for anchoring directed air bladder 20 on the abdomen to prevent pivotal movement when in inflated condition 23.

Referring to FIGS. 2A-2C, in use waist strap 16 is fed around the patient's body 12 with waist strap 16 lying above the iliac crests. Buckle 68 is then connected to secure waist strap 16 around the torso. Base plate 18 is positioned just left of midline at pressure point 14. The slack is then removed from waist strap 16 and the extra strap 16 is secured onto itself using hook and loop connectors 66. Compression latch 30 is operated from open position 42 to closed position 40 to further tighten waist strap 16. Air source 28 is applied to elbow connector valve 54, typically by screwing a threaded end of a $CO_2$ cartridge into a complementary threaded receiver on elbow connector valve 54. The cartridge 28 is screwed to its maximum depth to penetrate the cartridge. The cartridge is gently unscrewed slightly to release the compressed gas into directed air bladder 20 through inflation control valve 52. Pressure relief valve 56 may be operated to fine tune the application of force by directed air bladder 20. The flow of $CO_2$ can be stopped by screwing the cartridge into elbow connector valve 54. A pressure indicator may be incorporated on the device to warn if high pressure exists in the bladder or that the pressure is falling. Generally the bladder is inflated until the desired effect of cessation of bleeding occurs, or the desired effect of preload return to the heart is achieved. If a manual bulb pump 58 it is utilized generally in the same way as a blood pressure cuff.

While a preferred embodiment of the invention has been described using specific terms, such description is for illustrative purposes only, and it is to be understood that changes and variations may be made without departing from the spirit or scope of the following claims.

What is claimed is:

1. A method for applying a tourniquet to the abdominal region, comprising the steps of:
   a. providing an abdominal tourniquet comprising:
      i. an adjustable waist strap for securing said abdominal tourniquet around an abdomen;
      ii. a base plate carried by said waist strap having a width greater than said waist strap so that said base plate extends laterally outward from said waist strap to provide a stable base for positioning over a selected area of said abdomen;
      iii. an air bladder carried on a bottom side of said base plate having a deflated condition wherein said air bladder is collapsed against said base plate, and an inflated condition wherein said air bladder is expanded to extend outwardly from said bottom side of said base plate;
      iv. said air bladder having a generally elongated "V" shaped construction so that a wide end of said directed air bladder is generally carried on said bottom side of said base plate and an elongated narrow converging end of said directed air bladder forms an elongated edge positioned away from and parallel to said base plate, and,
      v. an air source operatively connected in fluid communication with said directed air bladder for operating said directed air bladder between said deflated condition and said inflated condition;
   b. securing said waist strap around an abdomen of a person, wherein said air bladder is in contact with the surface of said abdomen and positioned over the aorta at or above the umbilical region of said person;
   c. inflating said air bladder with said air source; and,
   d. wherein said inflation step causes said elongated edge of said directed air bladder to apply a constricting force against said abdomen such that said aorta is compressed to occlusion.

2. The method of claim 1, wherein said abdominal tourniquet includes a compression latch carried on said base plate operatively associated with said waist strap for tightening said waist strap around said abdomen.

3. The method of claim 2, wherein said compression latch includes a latch base mounted to a top side of said base plate in a fixed arrangement with a first distal end of said waist strap;
   a. a latch arm pivotally mounted to said latch base operable between a closed position adjacent said latch base and an open position extending upward from said latch base; and,
   b. a terminal pivot arm pivotally carried by said latch arm having a second distal end of said waist strap secured thereto, wherein said terminal pivot arm is moved from a relaxed position to a tightened position when said latch arm is operated from said open position to said closed position so that said waist strap is shortened to tighten around said abdomen.

4. The method of claim 3, wherein said abdominal tourniquet includes a foam pad carried on said bottom side of said base plate disposed between said air bladder and said base plate to cushion said base plate against said abdomen when said air bladder is in said deflated condition.

5. The method of claim 4, wherein said abdominal tourniquet includes a protective bladder sleeve surrounding said air bladder in both said inflated and collapsed conditions to resist puncture and protect against environmental exposure of said air bladder.

6. The method of claim 5, wherein said abdominal tourniquet includes an inflation control valve carried by said air bladder in fluid communication with said air source and an interior cavity of said air bladder for controlling the flow of air into and out of said air bladder.

7. The method of claim 6 wherein said inflation control valve extends though said base plate for cooperating with said air source on a top side of said base plate.

8. The method of claim 1, wherein said air source comprises a compressed gas cartridge and said abdominal tourniquet further includes a pressure relief valve operatively connected to said gas cartridge, and wherein said abdominal tourniquet includes an elbow connecting valve disposed between said inflation control valve and said compressed gas cartridge so that said compressed gas cartridge extends generally parallel to said base plate when engaged with said elbow connecting valve.

9. The method of claim 1, wherein said abdominal tourniquet further includes at least one guide marker carried on said base plate, said guide marker configured to direct a user of said abdominal tourniquet to position said base plate in an optimal location for pressing against said abdominal aorta upon inflation of said air bladder by aligning said marker along the midline of said person.

10. A method for using an abdominal aortic tourniquet to stop bleeding in a person comprising:
    a. providing an abdominal aortic tourniquet, comprising:
       i. an adjustable waist strap for securing said abdominal aortic tourniquet around an abdomen of a person;
       ii. a directed air bladder mounted to said waist strap having a generally cuneiform shaped construction having a narrow converging end extending away from said adjustable waist strap to form an edge parallel to said strap, said air bladder operable between a deflated condition wherein said directed air bladder is collapsed, and an inflated condition wherein said directed air bladder is expanded for exerting pressure by said edge into said abdomen; and,
       iii. an air source connected to said directed air bladder for operating said directed air bladder between said deflated condition and said inflated condition;

b. securing said waist strap around an abdomen of said person, wherein said directed air bladder is in contact with the surface of said abdomen and positioned over the abdominal aorta of said person above the inguinal area of said person;
c. inflating said directed air bladder with said air source; and
d. wherein said inflation step causes said edge to apply a deforming force across and against said aorta to occlude said same, and wherein said inflation step causes cessation of said bleeding at a location below and away from said point of aortic occlusion.

11. In a human experiencing a hemorrhage below the inguinal area of the body, an abdominal tourniquet adapted for achieving hemostasis at said hemorrhage site comprising:
a. an adjustable waist strap adapted for securing said abdominal tourniquet around an abdomen of said body;
b. a base plate carried by said waist strap and configured to provide a stable base therefrom, and wherein said base plate is adapted to be positioned over the abdominal aorta above the inguinal area of said body;
c. an air bladder carried on a bottom side of said base plate having a deflated condition wherein said air bladder is collapsed against said base plate, and an inflated condition wherein said air bladder is expanded to extend outwardly from said bottom side of said base plate toward said aorta; and,
d. said air bladder having an elongated "V" shape and configured so that when in said inflated condition a tip of said bladder penetrates said abdomen and occludes said aorta, and wherein said occlusion results in hemostasis at said hemorrhage site below the inguinal area of the body; and, wherein the tip of said air bladder comprises an elongate edge traversing the length of said bladder and generally equidistant from said base, wherein said elongated edge of the bladder is structured and dimensioned such that when said bladder is positioned over said aorta, said edge traverses said aorta to ensure occlusion of said aorta when said bladder is secured over the abdomen of said body and inflated, and,
e. an air source operatively connected to said air bladder for inflation of said same.

12. An abdominal tourniquet as recited in claim 11, further including a guide marker positioned on said base plate, said guide marker configured to direct a user of said tourniquet to position said tourniquet in an optimal occlusion location with respect to said aorta by aligning said marker along the midline of said body.

13. An abdominal tourniquet as recited in claim 12, wherein said air source comprises a compressed gas cartridge, and wherein said tourniquet includes an inflation control valve and a pressure relief valve.

14. An abdominal tourniquet as recited in claim 11, wherein said tourniquet is positioned such that said aortic occlusion results in hemostasis at a location different than said aorta occlusion location.

15. An abdominal tourniquet as recited in claim 11, wherein said bladder is sufficiently resilient such that said tip penetrates said abdomen to a sufficient depth to occlude said aorta when said bladder is in said expanded condition.

16. An abdominal tourniquet as recited in claim 11, wherein said tourniquet is positioned on said body such that said bladder occludes said aorta at a blood flow position upstream of and removed from said hemorrhage site.

17. An abdominal tourniquet, comprising:
a. an adjustable waist strap for securing said abdominal tourniquet around an abdomen;
b. a base plate carried by said waist strap and configured to provide a stable base therefrom, and wherein said base plate is positioned over the abdominal aorta above the inguinal area of the body;
c. an air bladder carried on a bottom side of said base plate having a deflated condition wherein said air bladder is collapsed against said base plate, and an inflated condition wherein said air bladder is expanded to extend outwardly from said bottom side of said base plate;
d. said air bladder having an elongated "V" shape and configured so that when in said inflated condition a tip of said bladder penetrates said abdomen and occludes said aorta; and, wherein the tip of said air bladder comprises an elongate edge traversing the length of said bladder and generally equidistant from said base, wherein said elongated edge of the bladder is structured and dimensioned such that when said bladder is positioned over said aorta, said edge traverses said aorta to ensure occlusion of said aorta when said bladder is secured over the abdomen of said body and inflated, and,
e. an air source operatively connected to and in fluid communication with said air bladder for operating said air bladder between said deflated condition and said inflated condition.

18. An abdominal tourniquet as recited in claim 17, wherein said tourniquet is positioned such that said tourniquet applies a minimum of 120 pounds per square inch effective force across said aorta when said bladder is in said expanded condition.

19. An abdominal tourniquet as recited in claim 18, wherein said air source comprises a compress gas cartridge, and wherein said tourniquet includes an inflation control valve and a pressure relief valve.

20. An abdominal tourniquet as recited in claim 17, wherein said bladder is positioned solely at or above the umbilical region of said body.

21. An abdominal tourniquet as recited in claim 17, wherein said tourniquet is positioned such that said aorta occlusion results in hemostasis at a location different than said aorta occlusion location.

22. In a human experiencing bleeding at or below the inguinal area of the body, a method for achieving homeostasis at said site of bleeding comprising the steps of:
a. providing a tourniquet comprising:
i. an adjustable waist strap adapted for securing said tourniquet around an abdomen of said body;
ii. a base plate carried by said waist strap and configured to provide a stable base therefrom;
iii. an air bladder carried on a bottom side of said base plate having a deflated condition wherein said air bladder is collapsed against said base plate, and an inflated condition wherein said air bladder is expanded outwardly from said bottom side of said base plate;
iv. said air bladder having an elongated "V" shape and configured for resilient expansion downward; and,
v. an air source operatively connected to and in fluid communication with said air bladder for operating said air bladder between said deflated condition and said inflated condition;
b. securing said waist strap around an abdomen of a person, wherein said air bladder is in contact with the surface of said abdomen and positioned over said aorta at or above the umbilicus region of said person;
c. inflating said air bladder with said air source;

d. wherein said inflation step forces the tip of said air bladder into the abdomen with sufficient force to occlude said aorta; and, e. wherein said inflation step causes homeostasis at said bleeding site below the inguinal area of the body.

23. The tourniquet method of claim 22, wherein said tip of said air bladder comprises an elongated edge traversing the length of said bladder and generally equidistant from said base, and wherein said inflation step causes said edge to traverse said aorta to ensure occlusion of said same when said tourniquet is secured over the abdomen of said body and inflated.

24. The tourniquet method of claim 23, wherein said inflation step causes aortic occlusion upstream from said site of bleeding.

25. The tourniquet method of claim 23, wherein said inflation step causes aorta occlusion at or above the abdominal aortic bifurcation in said abdomen.

26. The tourniquet method of claim 22, wherein said inflation step causes aorta occlusion at or above the abdominal aortic bifurcation in said abdomen.

27. The tourniquet method of claim 22, wherein said inflation step causes at least 230 mmHg of pressure to be applied within said bladder to ensure occlusion of said aorta.

28. The tourniquet method of claim 22, wherein said inflation step causes at least 120 lbs. per square inch of effective pressure applied to said aorta to ensure occlusion of said same.

\* \* \* \* \*